United States Patent [19]

Robertson

[11] Patent Number: 4,533,670
[45] Date of Patent: Aug. 6, 1985

[54] ANTI-CONVULSANT FLUORENYLALKYLIMIDAZOLE DERIVATIVES, COMPOSITIONS, AND METHOD OF USE

[75] Inventor: David W. Robertson, Indianapolis, Ind.

[73] Assignee: Eli Lilly and Company, Indianapolis, Ind.

[21] Appl. No.: 534,469

[22] Filed: Sep. 21, 1983

[51] Int. Cl.³ ............... A01N 43/50; A61K 31/415; C07D 233/60
[52] U.S. Cl. .................. 514/399; 548/336; 548/341
[58] Field of Search ............ 548/336, 341; 424/273 R; 514/399

[56] References Cited

U.S. PATENT DOCUMENTS

| | | | |
|---|---|---|---|
| 3,778,447 | 12/1973 | Draber | 260/309 |
| 3,826,837 | 7/1974 | Timmler | 424/273 |
| 4,036,970 | 7/1977 | Walker | 424/273 |
| 4,036,973 | 7/1977 | Walker | 424/273 |
| 4,036,974 | 7/1977 | Walker | 424/273 |
| 4,036,975 | 7/1977 | Walker | 424/273 |
| 4,038,409 | 7/1977 | Walker | 424/273 |
| 4,039,677 | 8/1977 | Walker | 424/273 |
| 4,039,705 | 11/1977 | Walker | 424/273 |
| 4,045,568 | 8/1977 | Walker | 424/273 |
| 4,150,153 | 4/1979 | Walker | 424/273 |
| 4,172,141 | 10/1979 | Walker | 424/273 |
| 4,239,765 | 12/1980 | Regel et al. | 424/269 |
| 4,275,071 | 7/1979 | Nardi | 424/273 |
| 4,375,474 | 3/1983 | Walker | 424/273 |

FOREIGN PATENT DOCUMENTS 0029355  5/1981  European Pat. Off. ............ 548/336

OTHER PUBLICATIONS

*J. Med. Chem.*, 24, 67 (1981), Keith A. M. Walker et al.
*Fed. Proc.*, 39, 316 (1980), Abstract No. 257.
*Fed. Proc.*, 42, 364 (1983), Abstract No. 424.
*J. Med. Chem.*, 24, 727 (1981), Dante Nardi et al.

*Primary Examiner*—Henry R. Jiles
*Assistant Examiner*—J. G. Mullins
*Attorney, Agent, or Firm*—Charles W. Ashbrook; Arthur R. Whale

[57] ABSTRACT

This invention provides for certain fluorenylalkyl imidazoles and their pharmaceutical formulations and their use as anticonvulsant agents.

20 Claims, No Drawings

ANTI-CONVULSANT FLUORENYLALKYLIMIDAZOLE DERIVATIVES, COMPOSITIONS, AND METHOD OF USE

BACKGROUND OF THE INVENTION

The sixteen anticonvulsant drugs marketed in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg./ml. Toxic effects such as nystagmus are seen at around 20 mcg./ml., ataxia is obvious at 30 mcg./ml., and lethargy is apparent at about 40 mcg./ml. See "The Pharmacological Basis of Therapeutics" (Gilman, Goodman, and Gilman, ed., 6th Ed., MacMillan Publishing Co., Inc., New York, New York (1980)), p. 455. In view of these facts, most epileptologists indicate there is a definite need for more selective and less toxic anticonvulsant drugs.

U.S. Pat. No. 4,150,153 teaches certain 1-(naphthylethyl)-imidazole derivatives which are taught to be useful as anticonvulsant and antisecretory agents. See also *J. Med. Chem.*, 24, 67 (1981). A variety of naphthyl- and phenylalkyl imidazoles are taught to be anticonvulsants in U.S. Pat. No. 4,275,071. See also *J. Med. Chem.*, 24, 727 (1981).

Certain fluorenylazolylmethylcarbinols are taught to be useful as antimycotic agents in U.S. Pat. No. 4,239,765. This publication teaches certain of the ketone compounds used in the present invention as intermediates to the claimed tertiary carbinol antimycotic agents.

SUMMARY OF THE INVENTION

This invention provides for compounds having the formula I

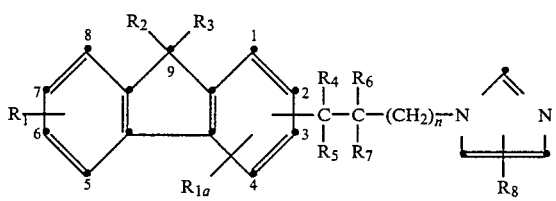

and pharmaceutically acceptable salts thereof, wherein:
 each of $R_1$ and $R_{1a}$ is independently hydrogen, methyl, or halo;
 each of $R_2$ and $R_3$ is independently hydrogen or methyl;
 one of $R_4$ and $R_5$ is hydrogen or $C_1$–$C_3$ alkyl and the other of $R_4$ and $R_5$ is —G—R, or when taken together $R_4$ and $R_5$ are —G—CH$_2$—CR$_a$R$_b$—(CH$_2$)$_p$—G—, where G is —O— or —S—, R is hydrogen, $C_1$–$C_3$ alkyl, or $R_9$—CO—, $R_9$ is phenyl, $C_1$–$C_3$ alkyl, or $C_3$–$C_7$ cycloalkyl, each of $R_a$ and $R_b$ is independently hydrogen or methyl, and p is 0 or 1;
 each of $R_6$ and $R_7$ is independently hydrogen, methyl, or ethyl;
 n is 0–2; and
 $R_8$ is hydrogen, methyl, or ethyl.

In addition to the compounds of Formula I, this invention also provides a method for treating and preventing convulsions in mammals in need of such treatment comprising administering to said mammal an effective amount of a compound of the Formula II

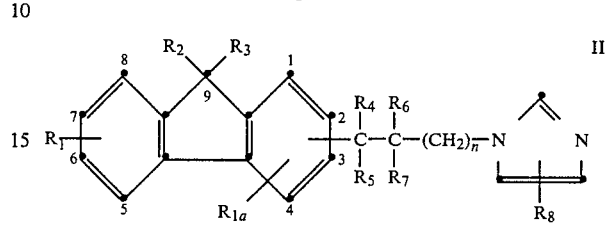

and pharmaceutically acceptable salts thereof, wherein:
 each of $R_1$ and $R_{1a}$ is independently hydrogen, methyl, or halo;
 each of $R_2$ and $R_3$ is independently hydrogen or methyl;
 one of $R_4$ and $R_5$ is hydrogen or $C_1$–$C_3$ alkyl and the other of $R_4$ and $R_5$ is —G—R, or when taken together $R_4$ and $R_5$ are keto or —G—CH$_2$—CR$_a$R$_b$—(CH$_2$)$_p$—G—, where G is —O— or —S—, R is hydrogen, $C_1$–$C_3$ alkyl, or $R_9$—CO—, $R_9$ is phenyl, $C_1$–$C_3$ alkyl, or $C_3$–$C_7$ cycloalkyl, each of $R_a$ and $R_b$ is independently hydrogen or methyl, and p is 0 or 1;
 each of $R_6$ and $R_7$ is independently hydrogen, methyl, or ethyl;
 n is 0–2; and
 $R_8$ is hydrogen, methyl, or ethyl.

According to a further aspect of the present invention, there is provided a pharmaceutical formulation which comprises as active ingredient a compound of Formula II as defined above associated with a pharmaceutically acceptable carrier.

DETAILED DESCRIPTION AND PREFERRED EMBODIMENT

The present invention relates to organic compounds that are useful for treating and preventing convulsions in mammals. A preferred group of compounds are the compounds of Formula II wherein:
 (a) $R_1$ is hydrogen,
 (b) $R_{1a}$ is hydrogen,
 (c) $R_2$ and $R_3$ are both hydrogen,
 (d) one of $R_4$ and $R_5$ is hydrogen or $C_1$–$C_3$ alkyl, especially methyl, and the other of $R_4$ and $R_5$ is —OH or —OCOR$_9$, or when taken together, $R_4$ and $R_5$ are keto or a ketal of the formula —O—CH$_2$—CHR$_b$—O—,
 (e) $R_6$ and $R_7$ are both hydrogen,
 (f) $R_8$ is hydrogen, and
 (g) n is 0.

Also preferred are those compounds of Formula II wherein the alkylimidazole functionality is substituted at the 1- or 2-position of the fluorene ring.

The following definitions refer to the various terms used throughout this disclosure. The term "halo" refers to fluoro, chloro, bromo, and iodo. The term "$C_1$–$C_3$ alkyl" refers to methyl, ethyl, n-propyl, and isopropyl. The term "$C_3$–$C_7$ cycloalkyl" refers to the saturated alicyclic rings of three to seven carbon atoms such as cyclopropyl, methylcyclopropyl, cyclobutyl, cyclopentyl, cyclohexyl, 4-methylcyclohexyl, cycloheptyl, and the like.

It is recognized that if $R_2$ is different from $R_3$, $R_4$ is different from $R_5$, $R_6$ is different from $R_7$, and/or if $R_a$ is different from $R_b$, various stereoisomers will exist. This invention is not limited to any particular isomer but includes all possible individual isomers and racemates of the compounds of this invention.

When $R_1$ is methyl or halo, the substituent may be at the 5-, 6-, 7-, or 8-position of the fluorene ring. Similarly, when $R_{1a}$ is methyl or halo, the substituent may be at the 1-, 2-, 3-, or 4-position other than where the alkylimidazole sidechain is attached. $R_8$ may be attached to any of the carbon atoms of the imidazole ring, i.e., the 2-, 4-, or 5-position.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, pyrosulfate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, hydroxybenzoate, methoxybenzoate, phthalate, terephthalate, benzenesulfonate, toluenesulfonate, chlorobenzenesulfonate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

Some of the compounds of this invention may be prepared by the reaction of a ketone derivative of the Formula III

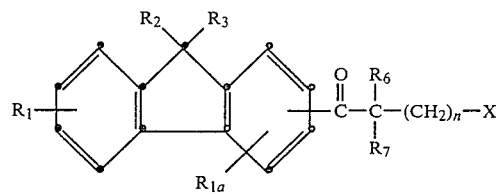

III where X is chloro, bromo, or iodo, with an imidazole derivative of the Formula IV.

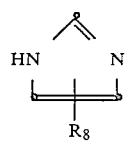

IV

This reaction provides the compounds of Formula II wherein $R_4$ and $R_5$ taken together are keto, referred to as compounds IIa.

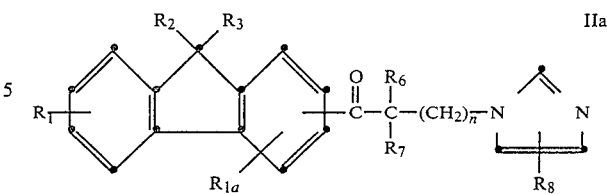

IIa

The reaction between compounds III and IV is usually performed with a molar excess of IV although other ratios are completely operative. The reaction is best carried out in a non-reactive solvent such as ketones, especially acetone or methyl ethyl ketone, or preferably dimethylformamide. The reaction may be carried out at temperatures from about 0° C. up to the boiling point of the reaction mixture. At the preferred temperature range of about 20°–30° C., the reaction is usually complete within 24 hours. The product thus obtained from the reaction may be purified by any of a number of methods known to those skilled in the art, such as chromatography or crystallization. The product may further be converted into a pharmaceutically acceptable salt by known methods; the addition of the acid to a hot solution of the product in a non-reactive solvent such as acetone or methanol is a particularly preferred method of preparing the salts.

The compounds of Formula IIa are also useful for preparing other compounds of this invention. For instance, compounds IIa wherein $R_6$ and/or $R_7$ are hydrogen may be alkylated with a methyl or ethyl halide to introduce those substituents. The alkylation reaction is performed according to standard procedures, usually employing equimolar amounts of IIa and the alkyl halide in a non-reactive solvent such as dimethylformamide and in the presence of one equivalent of a strong base such as sodium hydride. Either or both of the methyl or ethyl substituents may be introduced in this manner.

The alcohol, thiol, ketal, and thioketal derivatives may also be prepared from IIa. For example, the alcohol derivatives (II, one of $R_4$ and $R_5$ is hydrogen and the other is hydroxy) are prepared from the corresponding ketones by any of a number of reductive conditions. The most convenient and preferred method involves treating the ketone with sodium borohydride in a solvent such as methanol or ethanol.

The alcohol can be alkylated in the usual way to give the corresponding ether (II, where one of $R_4$ and $R_5$ is —O—($C_1$–$C_3$ alkyl) and the other of $R_4$ and $R_5$ is hydrogen) or can be acylated with the appropriate anhydride ($R_9$—CO—)$_2$O or acid halide $R_9$—COX in the presence of an acid scavenger such as pyridine to provide the corresponding ester derivatives (II, where one of $R_4$ and $R_5$ is —O—$COR_9$ and the other of $R_4$ and $R_5$ is hydrogen).

The thio compounds can be prepared from the corresponding alcohol compounds by first reacting with a thionyl halide and then treating with either sodium hydrosulfide or a sodium ($C_1$–$C_3$ alkyl)thiolate to give the corresponding compounds wherein one of $R_4$ and $R_5$ is —SH or —S—($C_1$–$C_3$ alkyl), respectively. The S-acyl derivatives can be prepared from the mercaptan compounds in the same way as previously described for the alcohol derivatives.

The ketal compounds are prepared from the ketones by heating with a compound in the usual manner. Thus, IIa is heated with a compound of Formula V $$H-G-CH_2-CR_aR_b-(CH_2)_p-G-H \qquad V$$

where G is oxygen in the presence of an acid such as p-toluenesulfonic acid, in a high boiling non-reactive solvent, such as benzene or toluene, with the concomitant removal of water. The thioketals can similarly be prepared from IIa and V (where G is sulfur), preferably in the presence of an acid such as methanesulfonic acid. The ketals, thioketals, alcohols, thiols, ethers, thioethers, and acyl derivatives may also be prepared by first modifying the ketone of intermediate III in the same manner as described for IIa and then reacting the derivative with IV in the usual way.

The tertiary carbinol compounds of Formula II where one of $R_4$ and $R_5$ is $C_1$-$C_3$ alkyl and the other of $R_4$ and $R_5$ is $-OH$ can be prepared directly by the addition of a $C_1$-$C_3$ alkyl Grignard reagent with ketone IIa, or indirectly by the addition of the Grignard reagent to Intermediate III and the subsequent reaction of the resulting tertiary carbinol with IV in the usual way. This carbinol may then be alkylated or acylated in the same manner as previously described. The corresponding thiol derivatives are prepared from the tertiary carbinol II by first converting the alcohol to a suitable leaving group, such as a halide, followed by subsequent displacement of the leaving group with R-SH using methods commonly known to those skilled in the art.

Intermediates III, IV, and V are commercially available, are known in the literature, or can be prepared by methods known in the art. For example, the halo-acylfluorenes III can be prepared by the direct haloacylation of the appropriate fluorene derivative VI

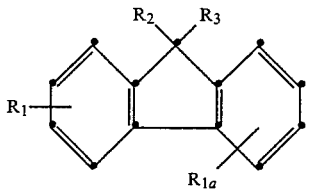

VI with an acid halide of the formula VII

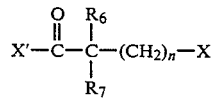

VII where X' is chloro, bromo, or iodo, according to the usual methods of acylation known in the art.

When n is 0, III may also be prepared by acetylating the fluorene compound and then introducing the halo substituent X by alpha-halogenation of the ketone functionality. As previously mentioned, the $R_6$ and $R_7$ substituents (other than hydrogen) can also be introduced alpha to the ketone.

Non-halogenated acetyl fluorenes may also be used as intermediates to the compounds of Formula II where n is 1. An acetyl fluorene is subjected to a Mannich reaction, preferably by heating with paraformaldehyde and a dialkylamine in a solvent such as ethanol, to provide the corresponding derivative related to compound III wherein n is 1 and X is dialkylamino. This intermediate is then transformed into a quaternary ammonium salt which is then heated with intermediate IV in a solvent such as dimethylformamide to provide the desired product II where n is 1. Other such leaving groups X and related transformations are apparent to those skilled in the art. Other, more indirect methods of preparing acyl fluorenes are also known in the literature.

The compounds II are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. Such compositions are prepared in a manner well known in the pharmaceutical art and comprise at least one active compound. Accordingly, the invention includes a pharmaceutical composition comprising as active ingredient a compound of Formula II or an acid addition salt thereof associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from about 5 to 500 mg., more usually 25 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following preparations and examples further illustrate the preparation of the starting materials, intermediates, and compounds of this invention. The examples are illustrative only and are not intended to limit the scope of the invention in any way.

PREPARATION 1

Bromomethyl 2-fluorenyl ketone

A slurry of 107.25 g of cupric bromide in 1,000 ml. of ethyl acetate was heated to reflux. A solution of 50.0 g. of 2-acetylfluorene in 500 ml. of chloroform was added over a 15-minute period. The reaction was heated at reflux for 3.5 hours and then filtered hot through a Celite pad. The filter cake was washed with ethyl acetate and the combined filtrate was evaporated in vacuo to provide 68.4 g. of the title intermediate which was used without further purification.

PREPARATION 2

Bromomethyl 1-fluorenyl ketone

A. Preparation of 1-acetylfluorene.

To a solution of 108 g. of 1-fluorenecarboxylic acid in 2 liters of dry tetrahydrofuran cooled to $-78°$ C. by means of an external dry ice/acetone bath were added 2 moles of methyl lithium (6 molar solution in diethyl ether). The reaction was stirred at room temperature for 3 hours and then poured into 3 liters of water. The layers were separated and the aqueous layer was extracted with ethyl acetate. The combined organic layers were dried over sodium sulfate and evaporated in vacuo. The residue was chromatographed over silica gel. The appropriate fractions were combined and evaporated to dryness. Recrystallization of the residue from ethyl acetate/hexane gave 1-acetylfluorene, m.p. 84°–87° C.

Analysis: $C_{15}H_{12}O$; Calc.: C, 86.51; H, 5.81; Found: C, 86.27; H, 5.81.

B. Preparation of bromomethyl 1-fluorenyl ketone.

The title intermediate was prepared from 1-acetylfluorene following the procedure of Preparation 1.

PREPARATION 3

Bromomethyl 4-fluorenyl ketone

A. Preparation of 4-fluorenecarboxylic acid.

One hundred grams of 9-fluorenone-4-carboxylic acid in 1 liter of ethyl acetate and 50 ml. of sulfuric acid were hydrogenated over one gram of 5% palladium-on-carbon at room temperature. The catalyst was removed by filtration and the filtrate was washed once with water. The organic layer was dried over magnesium sulfate and concentrated to dryness to provide 80 g. of the sub-title intermediate. The NMR and mass spectra were consistent with the structure of the desired intermediate.

B. Preparation of 4-acetylfluorene.

The acid chloride of 40 g. of 4-fluorenecarboxylic acid was prepared in the usual way. To this acid chloride in 60 ml. of dry tetrahydrofuran at $-78°$ C. were added 65 ml. of a 2.9 M solution of methylmagnesium chloride in tetrahydrofuran. After stirring at $-78°$ C. for ten minutes, 50 ml. of water were added. The reaction was allowed to warm to room temperature and concentrated in vacuo. The residue was taken up in water and extracted with ether. The ether was washed sequentially with 1N sodium hydroxide, water, and a saturated sodium chloride solution. The ether was dried over magnesium sulfate and concentrated in vacuo. The residue was crystallized from ethyl acetate/hexane to provide 35 g. of the subtitle intermediate as a low melting solid which was used without further purification.

C. Preparation of bromomethyl 4-fluorenyl ketone.

The title intermediate was prepared from 4-acetylfluorene following the procedure of Preparation 1.

PREPARATION 4

2-(Chloroacetyl)-7-methylfluorene

A. Preparation of 2-methylfluorene.

A solution of 20 g. of 2-fluorenecarboxaldehyde in 127 ml. of acetic acid was hydrogenated with 2 g. of 5% palladium-on-carbon and 1 ml. of hydrochloric acid at room temperature overnight. The reaction mixture was filtered and the filtrate was poured into water. The resulting solid was recovered by filtration and dissolved in ethyl acetate. The ethyl acetate solution was washed first with water and then with a saturated sodium chloride solution. The organic solution was dried over magnesium sulfate, filtered, and evaporated in vacuo to provide 17.98 g. of 2-methylfluorene, m.p. 90°–93° C.

B. Preparation of 2-(chloroacetyl)-7-methylfluorene.

A solution of 8.74 g. of 2-methylfluorene in 100 ml. of methylene chloride was cooled to 0° C. Anhydrous aluminum chloride (9.05 g.) was added and after 15 minutes of stirring, 5.4 ml. of chloroacetyl chloride were added dropwise to the solution. After stirring 15 minutes at 0° C. and 45 minutes at room temperature, the mixture was poured into 1 liter of ice and 200 ml. of hydrochloric acid. The layers were separated and the aqueous layer was extracted twice with methylene chloride. The combined organic layers were washed first with water and then with a saturated sodium chloride solution. The organic solution was dried over magnesium sulfate, filtered, and evaporated to dryness giving the desired title intermediate.

Following the same procedure, 2-(chloroacetyl)-7-bromofluorene was prepared from 2-bromofluorene.

PREPARATION 5

2-(Bromoacetyl)-9-methylfluorene

To a solution of 30 g. of fluorene in 500 ml. of anhydrous tetrahydrofuran cooled to $-78°$ C. by means of an external dry ice/acetone bath were added 120.5 ml. of a 1.6 M solution of n-butyl lithium in hexane. After stirring for 30 minutes, the reaction mixture was added to a $-78°$ C. solution of 56.2 ml. of methyl iodide in 60 ml. of anhydrous tetrahydrofuran. The reaction was stirred for 30 minutes at $-78°$ C. and then overnight at room temperature. The tetrahydrofuran was removed by evaporation and the residue was dissolved in ethyl acetate. The ethyl acetate was washed with water followed by a saturated sodium chloride solution, dried over magnesium sulfate, filtered and evaporated to dryness. Recrystallization from methanol provided 26.5 g. of 9-methylfluorene, m.p. 44°–45° C.

A solution of 10 g. of 9-methylfluorene in 300 ml. of tetrachloroethane was treated first with 10.5 g. of anhydrous aluminum chloride at 0° C. followed by the addition of 5.5 ml. of acetyl chloride. After stirring for 1 hour at 0° C., the reaction was poured into ice/hydrochloric acid. The aqueous material was extracted with methylene chloride. The organic extract was washed with water followed by a saturated sodium chloride solution. The organic solution was dried over magnesium sulfate, filtered, and evaporated to dryness. The residue was recrystallized from ethanol to provide 10.3 g. of 2-acetyl-9-methylfluorene, m.p. 114°–116° C.

Following the procedure of Preparation 1, 2-acetyl-9-methylfluorene was brominated to provide 2-(bromoacetyl)-9-methylfluorene which was used without purification.

Following the same procedure, fluorene was treated sequentially with two equivalents each of n-butyl lithium and methyl iodide to provide 9,9-dimethylfluorene. Acylation and bromination in the usual way provided the desired 2-(bromoacetyl)-9,9-dimethylfluorene intermediate which was used without purification.

EXAMPLE 1

1-(9H-fluoren-2-yl)-2-(2-methyl-1H-imidazol-1-yl)ethanone hydrochloride

A solution of 12.0 g. of 2-(bromoacetyl)fluorene in 150 ml. of dimethylformamide was added to an ice-cooled solution of 24 g. of 2-methylimidazole in 150 ml. of dimethylformamide. The mixture was allowed to warm to room temperature and was stirred overnight. The reaction mixture was poured into water containing one equivalent of sodium hydroxide. The resulting precipitate was filtered and the filtrate was extracted with ethyl acetate. The ethyl acetate solution was washed first with water and then with a saturated sodium chloride solution, dried over sodium sulfate, filtered, and evaporated in vacuo. The residue was combined with the filtered precipitate and dissolved in hot acetone. Three equivalents of hydrochloric acid were added and upon the addition of diethyl ether, 6.65 g. of the desired title product formed which were recovered by filtration, m.p. 275°–276° C. with decomposition.

Analysis: $C_{19}H_{16}N_2O.HCl$; Calc.: C, 70.26; H, 5.28; N, 8.62; Found: C, 70.43; H, 5.04; N. 8.73.

EXAMPLES 2–10

The following compounds were prepared from the corresponding imidazole derivative and the appropriate haloacetyl fluorene following the procedure of Example 1. Yields are expressed as percent molar yield.

2. 2-(2-ethyl-1H-imidazol-1-yl)-1-(9H-fluoren-2-yl)ethanone, m.p. 148°–150° C., 38.8% yield.

Analysis: $C_{20}H_{18}N_2O$; Calc.: C, 79.44; H, 6.00; N, 9.26; Found: C, 79.35; H, 6.20; N, 9.09.

3. 1-(9H-fluoren-2-yl)-2-(4-methyl-1H-imidazol-1-yl)ethanone hydrochloride, m.p. 265° C. with decomposition, 38.3% yield.

Analysis: $C_{19}H_{16}N_2O.HCl$; Calc.: C, 70.26; H, 5.28; N, 8.62; Found: C, 70.01; H, 5.31; N, 8.52.

4. 2-(1H-imidazol-1-yl)-1-(7-bromo-9H-fluoren-2-yl)ethanone hydrochloride, m.p. 282°–286° C., 35.9% yield.

Analysis: $C_{18}H_{13}BrN_2O.HCl$; Calc.: C, 55.48; H, 3.62; N, 7.19; Cl, 9.10; Br, 20.51; Found: C, 55.27; H, 3.74; N, 6.90; Cl, 8.96; Br, 20.23.

5. 2-(1H-imidazol-1-yl)-1-(9-methyl-9H-fluoren-2-yl)ethanone hydrochloride, m.p. 265°–266.5° C., 47.7% yield.

Analysis: $C_{19}H_{16}N_2O.HCl$; Calc.: C, 69.12; H, 5.48; N, 8.96; Found: C, 69.37; H, 5.38; N, 8.76.

6. 1-(9,9-Dimethyl-9H-fluoren-2-yl)-2-(1H-imidazol-1-yl)ethanone hydrochloride, m.p. 252°–253° C. with decomposition, 24.1% yield.

Analysis: $C_{20}H_{18}N_2O.HCl$; Calc.: C, 70.90; H, 5.65; N, 8.27; Cl, 10.46; Found: C, 70.57; H, 5.53; N, 7.98; Cl, 10.31.

7. 2-(1H-imidazol-1-yl)-1-(7-methyl-9H-fluoren-2-yl)ethanone hydrochloride, m.p. 263°–264.5° C., 46.9% yield.

Analysis: $C_{19}H_{16}N_2O.HCl$; Calc.: C, 70.26; H, 5.28; N, 8.62; Cl, 10.91; Found: C, 70.05; H, 5.33; N, 8.38; Cl, 10.80.

8. 2-(1H-imidazol-1-yl)-1-(9H-fluoren-2-yl)ethanone hydrochloride, m.p. 294°–296° C. with decomposition, 55% yield.

Analysis: $C_{18}H_{14}N_2O.HCl$; Calc.: C, 69.57; H, 4.87; N, 9.01; Cl, 11.41; Found: C, 69.57; H, 4.82; N, 8.79; Cl, 11.27.

9. 1-(9H-fluoren-1-yl)-2-(1H-imidazol-1-yl)ethanone hydrochloride, m.p. 274°–275° C., 30% yield.

Analysis: $C_{18}H_{14}N_2O.HCl$; Calc.: C, 69,57; H, 4.87; N, 9.01; Cl, 11.41; Found: C, 69.36; H. 4.59; N, 8.78; Cl, 11.33.

10. 1-(9H-fluoren-4-yl)-2-(1H-imidazol-1-yl)ethanone hydrochloride, m.p. 267.5°–268.5° C., 22% yield.

Analysis: $C_{18}H_{14}N_2O.HCl$; Calc.: C, 69.79; H, 4.56; N, 9.04; Cl, 11.44; Found: C, 68.52; H, 5.07; N, 8.81; Cl, 13.47.

EXAMPLE 11

1-(9H-fluoren-2-yl)-3-(1H-imidazol-1-yl)-1-propanone hydrochloride

A. Preparation of 3-(dimethylamino)-1-(9H-fluoren-2-yl)1-propanone hydrochloride.

A slurry of 2.0 g. of 2-acetylfluorene, 648 mg. of paraformaldehyde, and 1.57 g. of dimethylamine hydrochloride in 100 ml. of absolute ethanol and 1 ml. of hydrochloric acid was heated to reflux for 48 hours. Upon cooling, the title intermediate precipitated which was recovered by filtration yielding 1.85 g., m.p. 192°–193° C.

Analysis: $C_{18}H_{19}NO.HCl$; Calc.: C, 71.63; H, 6.68; N, 4.64; Found: C, 71.35; H, 6.64; N, 4.39.

B. Preparation of 1-(9H-fluoren-2-yl)-3-(1H-imidazol-1-yl)-1-propanone hydrochloride.

To a solution of 9.6 g. of 3-(dimethylamino)-1-(9H-fluoren-2-yl)-1-propanone in diethyl ether were added 10 ml. of methyl iodide. The resulting quaternary salt precipitated and was recovered by filtration. The 10.5 g. of precipitate were added to 12.3 g. of imidazole in 100 ml. of dimethylformamide. The solution was heated to 65° C. overnight and then poured into 1 liter of water. The resulting precipitate was recovered by filtration and crystallized from acetone/methanol/three equivalents of hydrochloric acid to provide 7.4 g. of the desired title product, m.p. 200°–202° C.

Analysis $C_{19}H_{16}N_2O.HCl$; Calc.: C, 70.26; H, 5.28; N, 8.62; Found: C, 69.98; H, 5.39; N, 8.50.

EXAMPLE 12

2-(1H-imidazol-1-yl)-1-(9H-fluoren-2-yl)-1-propanone hydrochloride

A solution of 15 g. of 2-(1H-imidazol-1-yl)-1-(9H-fluoren-2-yl)ethanone in 250 ml. of dimethylformamide was added to a slurry of 1.34 g. of sodium hydride in 50 ml. of dimethylformamide which was cooled to 0° C. The reaction was stirred at 0° C. for 30 minutes at which time 7.9 g. of methyl iodide were added. The reaction was stirred at room temperature for 1 hour, poured into water, and extracted with ethyl acetate. The organic layer was washed with water followed by a saturated sodium chloride solution, dried over sodium sulfate, and evaporated in vacuo. The resulting oil was chromatographed over silica gel to afford 7 g. of a brown oil. The hydrochloride salt was formed in the usual way giving a 44% yield of the desired title product, m.p. 237°–238.5° C.

Analysis $C_{19}H_{16}N_2O\cdot HCl$; Calc.: C, 70.26; H, 5.28; N, 8.62; Cl, 10.91; Found: C, 70.56; H, 5.40; N, 8.56; Cl, 10.58.

EXAMPLE 13

2-(1H-imidazol-1-yl)-1-(9H-fluoren-2-yl)-1-butanone hydrochloride

The title product was prepared in 48% yield from 2-(1H-imidazol-1-yl)-1-(9H-fluoren-2-yl)ethanone and ethyl iodide following the procedure of Example 12, m.p. 209°–211° C.

Analysis: $C_{20}H_{18}N_2O\cdot HCl$; Calc.: C, 70.90; H, 5.65; N, 8.27; Cl, 10.46; Found: C, 70.70; H, 5.64; N, 8.17; Cl, 10.17.

EXAMPLE 14

1-(9H-fluoren-2-yl)-2-(1H-imidazol-1-yl)-1-ethanol

Two grams of sodium borohydride were added in portions to a stirred suspension of ten grams of 2-(1H-imidazol-1-yl)-1-(9H-fluoren-2-yl)ethanone in 100 ml. of ethanol at room temperature. After one hour, the reaction mixture was poured into 700 ml. of water and the resulting precipitate was recovered by filtration. Crystallization of the solid from tetrahydrofuran/hexane provided 9.7 g. of the desired title product, m.p. 196°–199° C.

Analysis $C_{18}H_{16}N_2O$; Calc.: C, 78.24; H, 5.84; N, 10.14; Found: C, 78.04; H, 5.96; N, 9.93.

EXAMPLE 15

1-(9H-fluoren-2-yl)-3-(1H-imidazol-1-yl)-1-propanol

Following the procedure of Example 14, 1-(9H-fluoren-2-yl)-3-(1H-imidazol-1-yl)-1-propanone was reduced with sodium borohydride to provide a 72% yield of the title product, m.p. 143.5°–145.5° C.

Analysis: $C_{19}H_{18}N_2O$; Calc.: C, 78.59; H, 6.25; N, 9.65; Found: C, 78.63; H, 6.43; N, 9.59.

EXAMPLE 16

1-(9H-fluoren-2-yl)-2-(1H-imidazol-1-yl)-1-ethanol, benzoate ester hydrochloride A mixture of 9.0 g. of 1-(9H-fluoren-2-yl)-2-(1H-imidazol-1-yl)-1-ethanol and 9.59 g. of benzoic anhydride in 200 ml. of pyridine was heated at 55° C. for five hours. The mixture was poured into water and extracted with ethyl acetate. The organic layer was washed with a saturated sodium chloride solution, dried over sodium sulfate, and evaporated to dryness. Formation of the hydrochloride salt in the usual way and crystallization from acetone/diethyl ether provided 9.2 g. of the desired title product, m.p. 221°–222° C.

Analysis: $C_{25}H_{20}N_2O_2\cdot HCl$; Calc.: C, 72.02; H, 5.08; N, 6.72; Cl, 8.50; Found: C, 72.18; H, 5.12; N, 6.70; Cl, 8.58.

EXAMPLE 17

1-[2-(Ethylthio)-2-(9H-fluoren-2-yl)ethyl]-1H-imidazole hydrochloride

A solution of 4.69 g. of 1-(9H-fluoren-2-yl)-2-(1H-imidazol-1-yl)-1-ethanol in 150 ml. of thionyl chloride was stirred at 0° C. for 1 hour. The thionyl chloride was removed in vacuo and the residue was dissolved in 20 ml. of dimethylformamide. This solution was added to a solution of 108 millimoles of sodium ethane thiolate (prepared from ethanethiol and sodium hydride) in 100 ml. of dimethylformamide. The reaction was stirred for 30 minutes at room temperature and then poured into water. The aqueous layer was extracted with ethyl acetate. The organic extract was washed with water and a saturated sodium chloride solution, dried over sodium sulfate, and evaporated to dryness. Formation of the hydrochloride salt and crystallization from acetone/diethyl ether afforded 2.84 g. of the title product, m.p. 190°–193° C.

Analysis: $C_{20}H_{20}N_2S\cdot HCl$; Calc.: C, 67.30; H, 5.93; N, 7.85; Found: C, 67.51; H, 5.76; N, 7.84.

EXAMPLE 18

1-([2-(9H-fluoren-2-yl)-1,3-dioxolan-2-yl]methyl)-1H-imidazole

To a slurry of 10.0 g. of 2-(1H-imidazol-1-yl)-1-(9H-fluoren-2-yl)ethanone in 100 ml. of toluene were added 4.53 g. of ethylene glycol and 13.9 g. of p-toluenesulfonic acid. The mixture was heated overnight at reflux with the azeotropic removal of water. The reaction was poured into water and the resulting solid was removed by filtration. The solid was basified with 50 percent sodium hydroxide and extracted with ethyl acetate. The ethyl acetate was washed with water, followed by a saturated sodium chloride solution, dried over sodium sulfate, filtered, and evaporated in vacuo. The residue was crystallized from acetone to provide 8.64 g. of the title product, m.p. 163°–166° C.

Analysis: $C_{20}H_{18}N_2O_2$; Calc.: C, 75.45; H, 5.70; N, 8.80; Found: C, 75.26; H, 5.51; N, 8.55.

EXAMPLES 19–22

The following compounds were prepared according to the procedure of Example 18 using the appropriate diol and the corresponding ketone.

19. 1-([2-(9H-fluoren-2-yl)-4-methyl-1,3-dioxolan-2-yl]methyl)-1H-imidazole, m.p. 139°–144° C., 65% yield.

Analysis: $C_{21}H_{20}N_2O_2$; Calc.: C, 75.88; H, 6.06; N, 8.43; Found: C, 75.70; H, 6.35; N, 8.04.

20. 1-([2-(9H-fluoren-2-yl)-5,5-dimethyl-1,3-dioxan-2yl]methyl)-1H-imidazole, m.p. 187°–189° C., 71% yield.

Analysis: $C_{23}H_{24}N_2O_2$; Calc.: C, 76.64; H, 6.71; N, 7.77; Found: C, 76.53; H, 6.60; N, 7.59.

21. 1-([2-(9H-fluoren-2-yl)-1,3-dioxan-2-yl]methyl)-1H-imidazole hydrochloride, m.p. 259° C. with decomposition, 45.8% yield.

Analysis: $C_{21}H_{20}N_2O_2\cdot HCl$; Calc.: C, 68.38; H, 5.74; N, 7.54; Cl, 9.61; Found: C, 68.09; H, 5.78; N, 7.43; Cl, 9.48.

22. 1-(2-[2-(9H-fluoren-2-yl)-1,3-dioxolan-2-yl]ethyl)-1H-imidazole, m.p. 180°–185° C., 65.6% yield.

Analysis: $C_{21}H_{20}N_2O_2$; Calc.: C, 75.88; H, 6.06; N, 8.43; Found: C, 75.54; H, 5.80; N, 8.26.

EXAMPLE 23

1-([2-(9H-fluoren-2-yl)-1,3-dithiolan-2-yl]methyl)-1H-imidazole hydrochloride

To a solution of 10.0 g. of 2-(1H-imidazol-1-yl)-1-(9H-fluoren-2-yl)ethanone in 25 ml. of methanesulfonic acid were added 12.2 ml. of 1,2-ethanedithiol. After stirring overnight at room temperature, the reaction mixture was poured into water and the solution was made basic with sodium hydroxide. The resulting solid was recovered by filtration and crystallized from acetone/3 equivalents of hydrochloric acid to provide 10.16 g. of the title product, m.p. 248° C.

Analysis: $C_{20}H_{18}N_2S_2 \cdot HCl$; Calc.: C, 62.02; H, 4.95; N, 7.24; Found: C, 61.83; H, 4.74; N, 6.98.

EXAMPLE 24

1-(1H-imidazol-1-yl)-2-(9H-fluoren-2-yl)-2-propanol

A. Preparation of 1-chloro-2-(9H-fluoren-2-yl)-2-propanol.

To a solution of 15.0 g. of 2-(chloroacetyl)fluorene in 250 ml. of anhydrous tetrahydrofuran cooled to 0° C. by means of an external ice/ethanol bath were added three molar equivalents of methylmagnesium chloride (2.9M in tetrahydrofuran). The reaction was stirred at room temperature for two hours, and then cooled to 0° C. before the dropwise addition of 200 ml. of a 50% ammonium chloride solution. The reaction was extracted twice with ethyl acetate. The combined organic layers were washed with water followed by a saturated sodium chloride solution, dried over sodium sulfate, and evaporated to dryness. The residue was chromatographed over silica gel. The appropriate fractions were pooled and evaporated to provide 3.3 g. of the desired subtitle intermediate, m.p. 65°–68° C., which was used without further purification.

B. Preparation of 1-(1H-imidazol-1-yl)-2-(9H-fluoren-2-yl)-2-propanol.

To a slurry of 743 mg. of a 60% sodium hydride dispersion in oil in 50 ml. of dry dimethylformamide were added, in portions, 2.53 g. of imidazole. After hydrogen evolution had ceased, 3.2 g. of 1-chloro-2-(9H-fluoren-2-yl)-2-propanol in 50 ml. of dry dimethylformamide were added. The mixture was heated to 60° C. for one hour and then stirred overnight at room temperature. After heating an additional 2.5 hours at 85° C., the reaction mixture was poured into 700 ml. of water. The aqueous solution was extracted three times with ethyl acetate. The combined organic extracts were washed first with water followed by a saturated sodium chloride solution wash, dried over sodium sulfate, and evaporated to dryness. The residue was purified by chromatography over silica gel followed by crystallization from tetrahydrofuran/hexanes to provide 1.27 g. of the desired title product, m.p. 183°–184° C.

Analysis: $C_{19}H_{18}N_2O$; Calc.: C, 78.54; H, 6.25; N, 9.65; Found: C, 79.64; H, 6.38; N, 8.78.

The following formulation examples may employ as active compounds any of the pharmaceutical compounds of the invention.

EXAMPLE 25

Hard gelatin capsules are prepared using the following ingredients:

| | Quantity (mg./capsule) |
|---|---|
| Active compound | 250 |
| Starch dried | 200 |
| Magnesium stearate | 10 |

The above ingredients are mixed and filled into hard gelatin capsules in 460 mg. quantities.

EXAMPLE 26

A tablet formula is prepared using the ingredients below:

| | Quantity (mg./tablet) |
|---|---|
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 27

An aerosol solution is prepared containing the following components:

| | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 28

Tablets each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 29

Capsules each containing 80 mg. of medicament are made as follows:

| Active ingredient | 80 mg. |
|---|---|
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 30

Suppositories each containing 225 mg. of active ingredient are made as follows:

| Active ingredient | 225 mg. |
|---|---|
| Saturated fatty acid glycerides to | 2,000 mg. |

The active ingredient is passed through a No. 60 mesh U S. sieve and suspended in the saturated fatty acid glycerides previously melted using the minimum heat necessary. The mixture is then poured into a suppository mold of nominal 2 g. capacity and allowed to cool.

EXAMPLE 31

Suspensions each containing 50 mg. of medicament per 5 ml. dose are made as follows:

| Active ingredient | 50 mg. |
|---|---|
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of Formula II are anticonvulsant agents with a high therapeutic ratio and long half-life and are therefore useful in the treatment and/or prevention of convulsions in mammals. In particular, the compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the electroshock induced convulsion inhibition assay, the compound to be tested was dissolved in water (5%—sufficient hydrochloric acid was added for those compounds which were not isolated as a salt in order to effect dissolution) and administered by gavage to each of three Cox standard strain albino male mice (18-24 g.) at the dose level being investigated. Sixty to 240 minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound (for the particular time after administration of the compound) as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results are summarized in Table I as the $ED_{50}$'s at the optimal time after compound administration.

TABLE I $ED_{50}$ of Compounds of Formula II in the Electroshock Induced Convulsion Inhibition Assay

| Compound of Example No. | Time After Administration (minutes) | $ED_{50}$ (mg./kg. p.o.) |
|---|---|---|
| 1 | 60 | 210 |
| 2 | 120 | 188 |
| 3 | 60 | 90 |
| 4 | 120 | 79 |
| 5 | 120 | 33 |
| 6 | 60 | 48 |
| 7 | 120 | 68 |
| 8 | 180 | 25 |
| 9 | 120 | 20 |
| 10 | 60 | 44 |
| 11 | 60 | 19 |
| 12 | 90 | 35 |
| 13 | 60 | 50 |
| 14 | 60 | 22 |
| 15 | 60 | 33 |
| 16 | 60 | 32 |
| 17 | 60 | 44 |
| 18 | 240 | 23 |
| 19 | 120 | 21 |
| 20 | 120 | 65 |
| 21 | 60 | 32 |
| 22 | 60 | 26 |
| 23 | 120 | 41 |
| 24 | 120 | 14 |

I claim:

1. A compound of the Formula

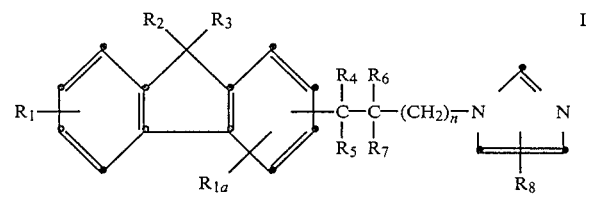

or a pharmaceutically acceptable salt thereof, wherein:
each of $R_1$ and $R_{1a}$ is independently hydrogen, methyl, or halo;
each of $R_2$ and $R_3$ is independently hydrogen or methyl;
one of $R_4$ and $R_5$ is hydrogen or $C_1$-$C_3$ alkyl and the other of $R_4$ and $R_5$ is —G—R, or when taken together $R_4$ and $R_5$ are —G—$CH_2$—$CR_aR_b$—($CH_2$)$_p$—G—, where G is —O— or —S—, R is hydrogen, $C_1$-$C_3$ alkyl, or $R_9$—CO—, $R_9$ is phenyl, $C_1$-$C_3$ alkyl, or $C_3$-$C_7$ cycloalkyl, each of $R_a$ and $R_b$ is independently hydrogen or methyl, and p is 0 or 1;

each of $R_6$ and $R_7$ is independently hydrogen, methyl, or ethyl;
n is 0–2; and
$R_8$ is hydrogen, methyl, or ethyl.

2. A compound of claim 1 wherein $R_8$ is hydrogen.

3. A compound of claim 2 wherein $R_6$ and $R_7$ are both hydrogen.

4. A compound of claim 3 wherein $R_4$ and $R_5$ taken together are —O—$CH_2$—$CHR_b$—O—.

5. A compound of claim 3 wherein one of $R_4$ and $R_5$ is —OH.

6. The compound of claim 5 which is 1-(1H-imidazol-1-yl)-2-(9H-fluoren-2-yl)-2-propanol or a pharmaceutically acceptable salt thereof.

7. The compound of claim 4 which is 1-([2-(9H-fluoren-2-yl)-4-methyl-1,3-dioxolan-2-yl]methyl)-1H-imidazole or a pharmaceutically acceptable salt thereof.

8. The compound of claim 5 which is 1-(9H-fluoren-2-yl)-2-(1H-imidazol-1-yl)-1-ethanol or a pharmaceutically acceptable salt thereof.

9. The compound of claim 4 which is 1-([2-(9H-fluoren-2-yl)-1,3-dioxolan-2-yl]methyl)-1H-imidazole or a pharmaceutically acceptable salt thereof.

10. A method for preventing convulsions in mammals in need of such treatment comprising administering to said mammal an anti-convulsant effective amount of a compound of the Formula or a pharmaceutically acceptable salt thereof, wherein:
each of $R_1$ and $R_{1a}$ is independently hydrogen, methyl, or halo;
each of $R_2$ and $R_3$ is independently hydrogen or methyl;
one of $R_4$ and $R_5$ is hydrogen or $C_1$–$C_3$ alkyl and the other of $R_4$ and $R_5$ is —G—R, or when taken together $R_4$ and $R_5$ are keto or —G—$CH_2$—$CR_aR_b$—$(CH_2)_p$—G—, where G is —O— or —S—, R is hydrogen, $C_1$–$C_3$ alkyl, or $R_9$—CO—, $R_9$ is phenyl, $C_1$–$C_3$ alkyl, or $C_3$–$C_7$ cycloalkyl, each of $R_a$ and $R_b$ is independently hydrogen or methyl, and p is 0 or 1;
each of $R_6$ and $R_7$ is independently hydrogen, methyl, or ethyl;
n is 0–2; and
$R_8$ is hydrogen, methyl, or ethyl.

11. A method according to claim 10 wherein one of $R_4$ and $R_5$ is —OH.

12. A method according to claim 10 wherein $R_4$ and $R_5$ taken together are keto.

13. A method according to claim 10 wherein $R_4$ and $R_5$ taken together are —O—$CH_2$—$CHR_b$—O—.

14. An anti-convulsant pharmaceutical composition which comprises an anti-convulsant effective amount of a compound of the formula or a pharmaceutically acceptable salt thereof, wherein:
each of $R_1$ and $R_{1a}$ is independently hydrogen, methyl, or halo;
each of $R_2$ and $R_3$ is independently hydrogen or methyl;
one of $R_4$ and $R_5$ is hydrogen or $C_1$–$C_3$ alkyl and the other of $R_4$ and $R_5$ is —G—R, or when taken together $R_4$ and $R_5$ are keto or —G—$CH_2$—$CR_aR_b$—$(CH_2)_p$—G—, where G is —O— or —S—, R is hydrogen, $C_1$–$C_3$ alkyl, or $R_9$—CO—, $R_9$ is phenyl, $C_1$–$C_3$ alkyl, or $C_3$–$C_7$ cycloalkyl, each of $R_a$ and $R_b$ is independently hydrogen or methyl, and p is 0 or 1;
each of $R_6$ and $R_7$ is independently hydrogen, methyl, or ethyl;
n is 0–2; and
$R_8$ is hydrogen, methyl, or ethyl;
in association with a pharmaceutically acceptable carrier or diluent.

15. A composition of claim 14 wherein one of $R_4$ and $R_5$ is —OH.

16. A composition of claim 14 wherein $R_4$ and $R_5$ taken together are keto.

17. A composition of claim 14 wherein $R_4$ and $R_5$ taken together are —O—$CH_2$—$CHR_b$—O—.

18. A composition of claim 15 wherein the compound is 1-(1H-imidazol-1-yl)-2-(9H-fluoren-2-yl)-2-propanol or a pharmaceutically acceptable salt thereof.

19. A composition of claim 16 wherein the compound is 1-(9H-fluoren-2-yl)-3-(1H-imidazol-1-yl)-1-propanone or a pharmaceutically acceptable salt thereof.

20. A composition of claim 17 wherein the compound is 1-([2-(9H-(fluoren-2-yl)-4-methyl-1,3-dioxolan-2-yl]methyl)-1H-imidazole or a pharmaceutically acceptable salt thereof.

* * * * *